United States Patent [19]
Kawai et al.

[11] Patent Number: 4,797,278
[45] Date of Patent: Jan. 10, 1989

[54] HYPOCHOLESTEROLEMICALLY AND/OR HYPOTRIGLYCERIDEMICALLY ACTIVE PRODUCTS AND THEIR USE

[75] Inventors: Yasuo Kawai, Atsugi; Kazunaga Yazawa, Sagamihara; Nobuo Suegara, Tsukui; Hirotaka Shimohashi, Kodaira, all of Japan

[73] Assignee: Kabushiki Kaisya Advance Kaihatsu Kenkyujo, Tokyo, Japan

[21] Appl. No.: 818,827

[22] Filed: Jan. 14, 1986

Related U.S. Application Data

[60] Division of Ser. No. 762,817, Aug. 5, 1985, Pat. No. 4,579,733, which is a continuation of Ser. No. 516,888, Jul. 25, 1983, abandoned.

[30] Foreign Application Priority Data

Aug. 6, 1982 [JP] Japan .................... 57-136241

[51] Int. Cl.$^4$ .................. A61K 35/74; C12N 1/20; C12R 1/46
[52] U.S. Cl. .................. 424/93; 435/885; 514/824
[58] Field of Search .................. 435/253, 885, 205; 424/93, 94; 514/824

[56] References Cited

U.S. PATENT DOCUMENTS

| | | | |
|---|---|---|---|
| 3,567,821 | 3/1971 | Nouvel | 424/93 |
| 4,190,649 | 2/1980 | Beljanski | 424/180 |
| 4,259,442 | 3/1981 | Gayral | 435/36 |
| 4,335,239 | 6/1982 | Beljanski | 536/27 |
| 4,389,396 | 6/1983 | Hinterland et al. | 424/92 |
| 4,448,768 | 5/1984 | Coleman et al. | 424/92 |
| 4,536,496 | 8/1985 | Shimizu et al. | 514/54 |
| 4,687,764 | 8/1987 | Kawai et al. | 514/54 |

FOREIGN PATENT DOCUMENTS

| | | | |
|---|---|---|---|
| A-101209 | 2/1984 | European Pat. Off. | 435/253 |
| A-115157 | 8/1984 | European Pat. Off. | 435/68 |
| A-132981 | 2/1985 | European Pat. Off. | 514/54 |
| 0186482 | 7/1986 | European Pat. Off. | 514/44 |
| 2106154 | 8/1972 | Fed. Rep. of Germany | 424/93 |
| 54-3100 | 1/1979 | Japan | 514/44 |
| 0122723 | 9/1980 | Japan | 424/93 |
| 56-12318 | 2/1981 | Japan | 424/92 |
| 0930107 | 7/1963 | United Kingdom | 424/93 |

OTHER PUBLICATIONS

Nord et al., "Formation of Glycoside-Hydrolases by Oral Streptococci"; *Archs. Oral Biol.,* vol. 18, pp. 391–402; 1973.

Watanabe et al.; "Studies on Streptococci"; *Microbiol. Immun.,* vol. 25, No. 3, pp. 257–269; 1981.

Kawai et al., "Studies on Streptococci"; *Microbiol. Immun.,* vol. 26, No. 5, pp. 363–373; 1982.

Kawai et al.; "Distribution & Colonization of Human Fecal Streptococci"; *Am. J. Clin. Nutr.,* Nov. 1980; vol. 33, pp. 2458–2461.

Hussain et al.; "Activation of Lipolytic Activity of *Streptococcus Faecalis* by Nitrosoguanidine"; *Folia Microbiol.;* vol. 21, pp. 73, 74, (1976).

Medical Tribune, vol. 25, No. 22, (Aug. 1, 1984), pp. 1 and 2.

Kawai et al.; "Intestinal Enzyme Activity in Germ–Free Conventional & Gnotobiotic Rats Associated with Indigenous Microorganisms"; *Infection & Immunity,* vol. 19, No. 3, pp. 771–778.

Kawai et al.; "Quantitative and Qualitative Alteration of Mucasal Alkaline Phosphatase by Intestinal Microbes in the Upper Digestive Tract of the Rat"; *Am. J. of Clin. Nutr.,* vol. 32, Jan. 1979, pp. 187–188.

Kawai et al.; "Intestinal Microflora and Aging: Age-Related Change of Lipid Metabolism in Germ–Free and Conventional Rats"; *Mech. of Aging & Dev.,* vol. 16, (1981); pp. 149–158.

Yazawa et al.; "Intestinal Microflora and Aging: Age-Related Change of Enzymes in the Liver and the Small Intestine of Germ-Free and Conventional Rats"; *Mech. of Aging & Dev.;* vol. 17, (1981), pp. 173–182.

Moore et al.; "Cell-Free Protein Synthesis: Effects of Age and State of Ribosomal Aggregation"; *Science,* vol. 154, Dec. 9, 1966, pp. 1350–1353.

Herson et al.; "Protein Synthesis in Cell-Free Extracts of *Streptococcus Faecalis*"; *J. Bacteriology,* Dec. 1969; pp. 1350–1354.

Rao et al.; "Influence of Milk and *Thermophilus Milk* on Plasma Cholesterol Levels and Hepatic Cholesterolgenesis in Rats"; *J. Food Sci.,* vol. 46, (1981), pp. 1339–1341.

Salvioli et al.; "Bile Acid Transformation by the Intestinal Flora and Cholesterol Saturation in Bile"; *Digestion,* vol. 23, pp. 80–88; (1982).

Rall, et al., "Human Apolipoprotein E," *J. Biol. Chem.,* vol. 257(8), pp. 4171–4178, (1982).

Slobodskaya, "Comparison of Hypocholesterolemic Effect ... ," Biol. Abstract, 76(10), (1983).

Bergy's Manual of Determinative Bacteriology, 8th Ed., Williams and Williams, 1974.

*Primary Examiner*—Elizabeth C. Weimar
*Attorney, Agent, or Firm*—Finnegan, Henderson, Farabow, Garrett & Dunner

[57] ABSTRACT

A bacterial cell product orally administered to lower serum cholesterol and/or triglyceride level in mammals obtained by cultivating a microorganism belonging to the genus Streptococcus and having a N-acetyl-$\beta$-D-glucosaminidase activity in an adequate culture medium therefor, and collecting the cultivated microorganism from the resultant culture.

3 Claims, No Drawings

HYPOCHOLESTEROLEMICALLY AND/OR HYPOTRIGLYCERIDEMICALLY ACTIVE PRODUCTS AND THEIR USE

This is a division of application Ser. No. 762,817, which is now U.S. Pat. No. 4,579,733 filed Aug. 5, 1985 which is a continuation of Ser. No. 516,888 filed July 25, 1983, now abandoned.

BACKGROUND OF THE INVENTION

1. Field of the Invention

The present invention relates to a hypocholesterolemic and/or hypotriglyceridemic active product, a process for producing the same, a pharmaceutical preparation containing the same, and novel strains of the genus Streptococcus suitably used in the production of the same.

2. Description of the Prior Art

As is well-known in the art, several pharmaceutical preparations such as clofibrate containing preparations have been proposed as a therapeutical or preventive medicine suitable for atherosclerosis or hyperlipidemia which is one of the so-called typical middle-aged or geriatric diseases. However, the desired purposes are not fully satisfied by these known medicines from the viewpoint of, for example, pharmacological effects and side-effects and, therefore, needs for developing more effective medicines have been remarkably increased.

SUMMARY OF THE INVENTION

Accordingly, an object of the present invention is to provide a novel bacterial cell product capable of effectively reducing the serum cholesterol and/or triglyceride level in mammals.

Another and further objects of the present invention are to provide a process for preparing a bacterial cell product capable of effectively reducing the serum cholesterol and/or triglyceride level in mammals, a pharmaceutical preparation containing the bacterial cell product, and a method for lowering serum cholesterol and/or triglyceride level in mammals.

A still further object of the present invention is to provide a novel strain having hypocholesterolemic and/or hypotriglyceridemic activity in mammals.

Other objects and advantages of the present invention will be apparent from the description set forth hereinbelow.

In accordance with the present invention, there is provided a process for preparing the bacterial cell product having the serum cholesterol and/or triglyceride level reducing activity in mammals comprising the steps of cultivating a microorganism belonging to the genus Streptococcus and having N-acetyl-$\beta$-D-glucosaminidase activity in an adequate culture medium therefor; and collecting the cultivated microorganism from the culture.

In accordance with the present invention, there is also provided a pharmaceutical composition for controlling the serum cholesterol and/or triglyceride level of patients comprising a preventively or therapeutically effective amount of living cells, dead cells, or a mixture thereof of a microorganism belonging to the genus Streptococcus and having hypocholesterolemic and/or hypotriglyceridemic activity in mammals, and a pharmaceutically acceptable carrier therefor.

In accordance with the present invention, there is further provided a pharmaceutical composition for controlling the serum LDL cholesterol level of patients comprising a preventively or therapeutically effective amount of living cells, dead cells, or a mixture thereof of a microorganism belonging to the genus Streptococcus and having the serum LDL cholesterol reducing activity in mammals, and a pharmaceutically acceptable carrier therefor.

In accordance with the present invention, there is still further provided a novel strain having hypocholesterolemic and/or hypotriglyceridemic activity in mammal and being at least one member selected from the group consisting of S. faecium FERM BP-296, S. faecalis FERM BP-297, S. avium FERM BP-298 S. salivarius FERM BP-299, S. durans FERM BP-300, S. mitis FERM BP-301 and S. equinus FERM BP-302.

In accordance with the present invention, there is still further provided a method for lowering the serum cholesterol and/or triglyceride level of mammals comprising orally administering to said mammals an effective amount of living cells, dead cells, or a mixture thereof of a microorganism belonging to the genus Streptococcus and having hypocholesterolemic and/or hypotriglyceridemic activity in mammals.

DESCRIPTION OF THE PREFERRED EMBODIMENTS

The present inventors have found that various living cells and dead cells of microorganisms belonging to the genus Streptococcus can effectively reduce the serum cholesterol and/or triglyceride level in mammals These microorganisms derived from so-called gastrointestinal bacteria are substantially nontoxic when orally administered, and the microorganisms having specific morphological characteristics have excellent ability to adhere to intestinal epithelial cells and the extremely high pharmacological activity.

The types and morphological characteristics, the screening methods, the ability to adhere to intestinal epithelial cells, the preparation methods of strains, and the pharmacological effects of the microorganisms according to the present invention will now be shown in detail hereinbelow.

Microorganisms

Microorganisms suitable for use in the preparation of the bacterial cell product according to the present invention are those belonging to the genus Streptococcus and characterized by the cultivated supernatant liquid thereof having N-acetyl-$\beta$-glucosaminidase activity. Typical examples of such microorganisms have been deposited since July 15, 1982 in the Fermentation Research Institute (FRI) in Japan (all the numbers quoted as "FERM-P" in Table 1 refer to the deposition numbers of said Institute) and transferred to the Fermentation Research Institute (FRI) (i.e., International Depository Authority under Budapest Treaty in Japan) as the following FERM-BP deposition numbers in Table 1 under Budapest Treaty on the International Recognition of the Deposit of Microorganisms for the Purpose of Patent Procedure:

TABLE 1

| Name of strain | Deposition number |
| --- | --- |
| Streptococcus faecium ADV 1009 | FERM P-6624 FERM BP-296 |
| Streptococcus faecalis ADV 9001 | FERM P-6625 FERM BP-297 |
| Streptococcus avium AD 2003 | FERM P-6626 FERM BP-298 |
| Streptococcus salivarius ADV 10001 | FERM P-6627 FERM BP-299 |
| Streptococcus durans ADV 3001 | FERM P-6628 FERM BP-300 |

TABLE 1-continued

| Name of strain | Deposition number |
|---|---|
| *Streptococcus mitis* ADV 7001 | FERM P-6629 FERM BP-301 |
| *Streptococcus equinus* ADV 8001 | FERM P-6630 FERM BP-302 |

Microbiological Properties of Microorganism

Microorganisms utilizable in the present invention are microbiologically characterized by having N-acetyl-$\beta$-D-glucosaminidase activity ("enzyme A activity" hereinbelow). As mentioned hereinbelow, it is estimated that this enzyme activity is correlated to some extent to high ability to adhere of the microorganisms according to the present invention to intestinal epithelial cells.

Enzyme A Activity Determination Method

The enzyme activity can be determined as follows:

A strain tested is inoculated into 5 ml of a Todd-Hewitt broth medium*[1] and, then, is stationarily cultivated at 37° C. for 20 hours under an aerobic condition to prepare a culture fluid containing $10^9$ living cells/ml. The cells are collected by centrifugation of the culture fluid at 3,000 rpm for 15 minutes. The separated cells are washed twice with 0.1M phosphate buffer solution (pH 6.5). The centrifuged cells are suspended in the same buffer solution to prepare an analyte sample containing $10^{10}$ living cells/ml.

*[1] A Todd-Hewitt broth medium is prepared by dissolving 30 g of a freeze dried powder of a mixture having the following composition (parts by weight) in 1 liter of distilled water:

| Composition | Parts |
|---|---|
| Bovine cardiac extract | 500.0 |
| Peptone | 20.0 |
| Dextrose | 2.0 |
| Sodium chloride | 2.0 |
| Disodium phosphate | 0.4 |
| Sodium carbonate | 2.5 |

(pH 7.8, heat sterilization at 121° C. for 15 min; Updyke et al., Applied Microbiol., 2: 117, 1954: Catalogue No. BBL 11735)

One tenth ml of the sample is then mixed with 0.3 ml of a 5 mM p-nitrophenyl-N-acetyl-$\beta$-D-glucosaminide substrate solution (0.1M phosphate buffer solution at pH 6.5) and the mixture is allowed to react at 37° C. for 20 minutes. 2.5 ml of 0.25N aqueous $Na_2CO_3$ solution is added to the reaction mixture and, then, is allowed to stand at room temperature for 30 minutes. The mixture is separated by centrifugation at 3,200 rpm for 20 minutes to remove the bacterial cells. The concentration of free p-nitrophenol is colorimetrically and quantitatively determined at 420 nm ("mM/mg protein" unit). The control analysis is carried out by using 0.1 ml of the above sample after heat-treatment at 100° C. for 15 minutes (this is also the same hereinbelow). The determination of a protein content in the above sample is measured by a method according to Lowry et al. J. Biol. Chem. 193: 265 (1951).

General Microbiological Characteristics

General microbiological characteristics, other than the above-mentioned characteristics, of the microorganisms in the present invention are the same as those of known microorganisms belonging to the identical class. That is, the general microbiological characteristics, cultivation methods and other properties correspond to those described in the following articles:

(1) Bergey's Manual of Determinative Bacteriology, 8th ed., 490–509 (1974)
(2) Int. J. Syst. Bact. 16 114 (1966)
(3) Microbiol. Immunol. 25 (3), 257–269 (1981)
(4) J. Clin. Pathol. 33 53–57 (1980)
(5) J. General Microbiol., 128 713–720 (1982)
(6) Applied Microbiol., 23 (6) 1131–1139 (1972)

The typical biological properties of the above-exemplified strains according to the present invention. can be summarized as follows:

TABLE 2

| Characteristics | ADV 1009 | ADV 9001 | AD 2003 | ADV 10001 | ADV 3001 | ADV 7001 | ADV 8001 |
|---|---|---|---|---|---|---|---|
| Shape of cell | ← spheroid → | | | | | | |
| Gram stain | + | + | + | + | + | + | + |
| Hemolysis | α | α | α | α | α | α | α |
| Growth at 10° C. | + | + | ± | − | + | − | − |
| Growth at 45° C. | + | + | + | ± | + | ± | + |
| Growth at 50° C. | + | − | − | − | + | − | − |
| Thermal resistance at 60° C. for 30 min | + | + | + | − | + | − | − |
| Growth in culture medium at pH 9.6 | + | + | + | − | + | − | − |
| Methylene blue reduction ability | + | + | − | − | + | − | − |
| Liquefaction of gelatin | − | − | − | − | − | − | − |
| Growth in culture medium containing NaCl (6.5%) | + | + | − | − | + | − | − |
| Growth in culture medium containing bile (40%) | + | + | + | − | + | − | + |
| Productivity of ammonia | + | + | ND | − | + | ± | − |
| Hydrolysis of hippuric acid | − | ± | − | − | + | − | − |
| Growth in culture medium containing tellurite | − | + | − | ND | − | ND | − |
| Growth in culture medium containing TTC*[1] | − | + | − | ND | − | ND | − |
| Acid production from carbon source | | | | | | | |
| Glucose | + | + | + | + | + | + | + |
| Esculin | ± | + | + | + | ± | ND | + |
| Inulin | − | − | − | + | − | − | ± |
| Lactose | + | + | + | ± | + | ± | − |
| Glycerol | − | + | ± | − | − | − | − |

TABLE 2-continued

| Characteristics | Strains | | | | | | |
|---|---|---|---|---|---|---|---|
| | ADV 1009 | ADV 9001 | AD 2003 | ADV 10001 | ADV 3001 | ADV 7001 | ADV 8001 |
| Arabinose | + | − | + | − | − | − | − |
| Melezitose | − | + | ± | ND | − | ND | − |
| Sorbitol | − | + | + | − | − | − | − |
| Antigenic group | D | D | Q(D) | K | D | − | D |

*[1] 2,3,5-triphenyltetrazolium chloride

The cultivation of these microorganisms is conventional as mentioned above. For example, the bacterial cells can be collected by stationarily cultivating in a Rogosa broth medium having the following composition under an aerobical condition, and can be harvested by the centrifugation of the culture.

Composition of Rogosa Broth Medium

| | |
|---|---|
| Trypticase | 10 g |
| Yeast extract | 5 g |
| Tryptose | 3 g |
| $K_2HPO_4$ | 3 g |
| $KH_2PO_4$ | 3 g |
| Triammonium citrate | 2 g |
| Tween 80 | 1 g |
| Glucose | 20 g |
| Cysteine hydrochloride | 0.2 g |
| Salt solution*[1] | 5 ml |
| Distilled water | to 1 liter |
| (pH 7, heat sterilization at 121° C. for 15 minutes) | |
| *[1] $MgSO_4.7H_2O$ | 11.5 g |
| $FeSO_4.7H_2O$ | 0.68 g |
| $MnSO_4.2H_2O$ | 2.4 g |
| Distilled water | 100 ml |

The resultant cells can be directly used as a pharmaceutical agent in the form of living cells or dead cells obtained by, for example, heat-treatment, or in the form of the cells destructed by, for example, ultrasonic treatment. The term "dead cells" used herein means the entire portions or partial portions of the above-mentioned destructed cells.

The dead cells can be also used as a starting material for fractionating, extracting, and purifying active elements contained therein. This is the reason why the desired pharmacological activities (i.e., hypocholesterolemic and/or hypotriglyceridemic activity in mammals) are based on substance components contained in the cells, namely because not only the living cells but also the dead cells have the pharmacological activities.

Screening Methods

The screening of the microorganisms can be carried out by a method of Watanabe, T., et al., Studies on streptococci. I. Distribution of fecal streptococci in man. Microbiol. Immunol. 25 257–269 (1981).

That is, as mentioned in this literature, 10 fold diluted feces obtained from healthy adults were smeared on KMN agar and SF agar and were aerobically cultivated at 37° C. for 48 to 72 hours. The formed colonies were counted and were randomly isolated. The colony type and catalase negative and Gram positive spherical strains were determined and the isolates were identified and classified by examining physiological, biochemical and serological properties. Then, the enzyme A activity and pharmacological effects of many identified strains on mammals thus obtained were determined. Thus, the microorganisms used in the present invention were finally screened.

Adhesion Ability to Intestinal Epithelial Cells

The microorganisms used in the present invention have a useful property, that is, remarkably high ability to adhere to the epitherial cells of the intestine such as ileum and rectum of humans. Especially when the living cells of the microorganisms are used for administration, various pharmacological effects such as the below-mentioned anti-athorosclerotic effects in addition to, for example, well-known alleviation effects on gastrointestinal disorders can be efficiently continued. That is, it is known that beneficial bacteria colonize the appropriate areas of the intestines, depending upon the varieties of the bacteria. One of the important factors for the colonization of the bacteria can be the adhesion of bacteria to the intestinal epithelium. Accordingly, it is considered that the bacteria possessing an ability to adhere to intestinal epithelia are more likely to multiple in the intestine and, therefore, the hosts can be effectively influenced by the characteristics of the useful bacteria per se or their action. Hence, by the use of the microorganisms of the present invention, various useful effects on hosts such as anti-atherosclerotic effects and the alleviation effects on gastrointestinal disorders can be strengthened.

The assay method for the bacterial ability to adhere to host epithelial cells used in the examples hereinbelow is summarized as follows:

Adhesion-Assay Method

Normal gastrointestinal epithelial cells of animals and the tissues obtained from patients were scraped off, washed to remove gastrointestinal contents and suspended in phosphate buffered saline (PBS) ($10^6$ cells/ml). This cell suspension was placed on a slide glass (0.025 ml/0.5 cm$^2$) and was air dried. Then, the epithelial cells on the slide glass were flooded with 0.025 ml of previously prepared bacterial suspension ($10^{10}$/ml). After allowing to stand at 37° C. for 10 minutes, the slide glass was washed three times with phosphate buffered saline to remove unattached bacteria to the epithelial cells. The bacteria adhered to the epithelial cells were stained with Gram stain and the number of the adhered bacteria was counted microscopically.

This method is further referred in detail to Suegara, N., et al., Infect. Immun. 12 (1), 173–179 (1975).

Preparation of Bacterial Cells

The living cells and dead cells of the microorganisms used in the present invention, suitable for use as an anti-atherosclerotic agent, are typically prepared as follows:

1. Preparation Example of the Living Cells

Each strain of the above-mentioned microorganisms is inoculated into 5 liter of the above-mentioned Rogosa broth medium and, then, is stationarily cultivated under an aerobic condition at 37° C. for 5 hours to yield the subsequent culture broth containing $10^9$/ml of the living cells. The microorganisms are harvested by continuous centrifugation at 12,000 rpm. The bacterial cells are washed with physiological saline and, then, are suspended in physiological saline to obtain 50 ml of the cell suspension containing $10^{11}$ cells/ml.

2. Preparation Example of the Dead Cells

The living cells obtained as mentioned in the above Example are further washed twice with physiological saline (0.85% NaCl solution) and, then, are suspended in the same solution. Fifty ml of the cell suspension was thus obtained, and is heated at 115° C. for 10 minutes to form the desired cell suspension containing the dead cells.

Pharmacological Actions

1. Pharmacological effects (a) As shown in each example hereinbelow, the bacterial cell products obtained from the above-mentioned microorganisms of the present invention can make extremely effective reduction of a serum cholesterol and/or triglyceride level in mammals. Accordingly, the bacterial cell products according to the present invention are useful as a therapeutical or preventive medicine for diseases closely related to atherosclerosis, hyperlipidemia, hyperlipoproteinemia, xanthomatosis, cholecystolithiasis, hypertension, diabetes, and others.

The term "a hypocholesterolemic and/or hypotriglyceridemic activity" used herein, especially as related to examples 3 and 5 hereinbelow means the activity of reducing a serum cholesterol and/or triglyceride level over about 20% as compared with a control in mammals. This is because the reducing rate of over about 20% is remarkably pharmacological effects, since standard deviations in these animal tests are deemed to be generally ±10%.

(b) As also shown in examples hereinbelow, the cell products obtained from the above-mentioned microorganisms of the present invention have a clinically important pharmacological activity that the level of low density lipoprotein (LDL) cholesterol in the serum cholesterol can be especially effectively reduced.

(c) The pharmaceutical composition according to the present invention can be generally applied in a dosage of $10^7$ to $10^{15}$ cells/kg body weight, more desirably $10^9$ to $10^{12}$ cells/kg body weight by, for example, an oral administration. The pharmaceutical composition according to the present invention can be in the form of, for example, suspensions in physiological saline solutions, powder, granules, tablets, and capsules. The pharmaceutical composition according to the present invention can be optionally prepared by using conventional appropriate carriers, bulk fillers, and diluents and so on.

2. Acute Toxicity

As shown in the examples hereinbelow, an $LD_{50}$ of the living cells according to the present invention is $8.9 \times 10^8$ to $1.3 \times 10^{10}$ cells/mouse (intraperitoneal administration) and that of the dead cells according to the present invention is more than $6 \times 10^{13}$ cells/mouse (intraperitoneal administration).

Both the living and dead cells according to the present invention are substantially nontoxic an oral administration.

EXAMPLES

The present invention will now be further shown by, but is by no means limited to, the following examples.

EXAMPLE 1

The enzyme A activities of the typical examples of the strains according to the present invention were determined according to the above-mentioned enzyme A activity determination method. The results are shown in Table 3.

As a control, the data of *Streptococcus faecalis* ATCC 19433 and *Streptococcus faecium* ATCC 19434 described in "THE AMERICAN TYPE CULTURE COLLECTION" Catalogue of Strains I, 14th ed., 160–161 (1980) are also shown in Table 3.

TABLE 3

| Strains | Enzyme A activity[*1] |
| --- | --- |
| ADV 1009 | 5.35 |
| ADV 9001 | 4.95 |
| AD 2003 | 3.83 |
| ADV 10001 | 3.14 |
| ADV 3001 | 2.93 |
| ADV 7001 | 4.37 |
| ADV 8001 | 3.03 |
| ATCC 19433 | n.d.[*2] |
| ATCC 19434 | n.d.[*2] |

[*1]mM/mg protein
[*2]Not detectable

EXAMPLE 2

The adhesion abilities to human ileal epithelial cells of the typical examples of the strains used in the present invention were assayed by the above-mentioned adhesion-assay method. The results are shown in Table 4.

As controls, the data of the above-mentioned ATCC strains and the average of 20 strains each of various bacterial species which have no substantial enzyme A activity obtained in the course of the screening are also shown in Table 4.

TABLE 4

| Strains | Adhered bacterial cell number/$6 \times 10^{-7}$ cm$^2$ |
| --- | --- |
| ADV 1009 | 13.1 |
| ATCC 19434 | 1.2 |
| ADV 9001 | 15.0 |
| ATCC 19433 | 1.7 |
| AD 2003 | 5.5 |
| *S. avium** | ~0 |
| ADV 10001 | 13.5 |
| *S. salivarius** | 1.5 |
| ADV 3001 | 3.8 |
| *S. durans** | ~0 |
| ADV 7001 | 12.5 |
| *S. mitis** | 2.6 |
| ADV 8001 | 12.6 |
| *S. equinus** | 0.9 |

*Average of 20 examples of strains having no substantial enzyme A activity

Example 3

Physiological saline suspension samples containing living cells of various strains of the genus Streptococcus were prepared by the above-mentioned living cell preparation method. These samples were orally administered at a dosage of $10^{11}$ cells to conventional rats (18 week-old males, average body weight of 246 g, 15 males in each group) and germfree mice (18 week-old males, average body weight of 30 g, 10 males, in each group). Thereafter, the rats and mice were bred for 8 to 12 weeks. Then, arterial blood was collected from the abdominal aorta of these rats and mice and the serum samples were separated by centrifugation from the whole blood.

The cholesterol level, triglyceride level, and LDL cholesterol level were determined by using Choleskit (Trademark, manufactured by Kanto Kagaku K.K., Zurkowski method), Triglyceride-Test Wako (Trademark, Wako Pure Chemical Industries, LTD., acetylacetone extraction method), and β-Lipoprotein-Test Wako (Trademark, Wako Pure Chemical Industries, LTD., Hoeflmayer-Fried method), respectively.

The results are shown in Table 5A (cholesterol level, Table 5B (LDL cholesterol level), and Table 6 (triglyceride level). The values listed in these tables are those (%) when the values of the control groups to which no sample is dosed are 100%. The composition (% by weight) of the diet is shown in Table 7.

TABLE 5A

| Strains | Rat 12 week | Mouse 12 week | Mouse 8 week |
|---|---|---|---|
| S. faecium ADV 1009 | 60.4 | 65.4 | — |
| S. faecalis ADV 9001 | 57.1 | — | 58.9 |
| S. avium AD 2003 | 66.3 | 55.1 | — |
| S. salivarius ADV 10001 | 62.9 | — | 59.6 |
| S. durans ADV 3001 | 57.3 | 47.6 | — |
| S. mitis ADV 7001 | 63.1 | — | 51.5 |
| S. equinus ADV 8001 | 65.2 | 55.4 | — |
| S. faecalis ATCC 19433 | 81.4 | — | — |
| S. faecium ATCC 19434 | — | 79.3 | — |

TABLE 5B

| Strains | Rat 12 week | Mouse 12 week | Mouse 8 week |
|---|---|---|---|
| S. faecium ADV 1009 | 57.3 | 52.7 | — |
| S. faecalis ADV 9001 | 64.1 | — | 60.6 |
| S. avium AD 2003 | 60.4 | 55.9 | — |
| S. salivarius ADV 10001 | 68.1 | — | 62.9 |
| S. durans ADV 3001 | 54.7 | 48.2 | — |
| S. mitis ADV 7001 | 62.3 | — | 55.4 |
| S. equinus ADV 8001 | 70.4 | 59.4 | — |
| S. faecalis ATCC 19433 | 83.1 | — | — |
| S. faecium ATCC 19434 | — | 81.1 | — |

TABLE 6

| Strains | Rat 12 week | Mouse 12 week | Mouse 8 week |
|---|---|---|---|
| S. faecium ADV 1009 | 33.9 | — | 51.2 |
| S. faecalis ADV 9001 | — | 35.5 | — |
| S. avium AD 2003 | 24.4 | — | 44.5 |
| S. salivarius ADV 10001 | — | 47.2 | — |
| S. durans ADV 3001 | 31.4 | — | — |
| S. mitis ADV 7001 | 51.5 | — | 57.2 |
| S. equinus ADV 8001 | — | 57.6 | — |
| S. faecalis ATCC 19433 | — | 89.9 | — |
| S. faecium ATCC 19434 | 83.0 | — | — |

TABLE 7

| Composition | wt. % |
|---|---|
| Casein | 20 |
| Soybean oil | 10 |
| Wheat starch | 61 |
| Minerals | 4 |
| Vitamin mixture | 2 |
| Powdered filter paper | 3 |

Example 4

Tissue thin sections of the intestines such as ileum of each animal used in Example 3 were made and stained by Gram stain. The Gram-stained thin sections were micrographically observed. As a result, it was found that the strains used in the present invention colonized the intentional mucosae at a remarkably high density, as compared with those in the control ATCC strains.

Example 5

Heat-treated bacterial cell suspensions of various microorganisms of the genus Streptococcus were prepared by the above-mentioned dead cell preparation method. These samples were orally administered at a daily dosage of $10^{11}$ cells per rat for 12 weeks to conventional rats (18 week-old males, average body weight of 238 g, 15 males in each group) and conventional and germfree mice (18 week-old males, average body weight of 31 g, 10 males in each group).

The cholesterol level, LDL cholesterol level, and triglyceride level were determined by the same methods as in Example 3. The results are shown in Table 8A, Table 8B, and Table 9, respectively.

The "cholesterol-loaded" and "fructose-loaded" in these Tables mean the addition of 1% cholesterol into the above-mentioned diet and the substitution of fructose for the total amount of the wheat starch in the above-mentioned diet. The values listed in Tables are those (%) when the values of the no dosage control groups are 100%.

TABLE 8A

| Strains | Germ-free mouse | Conventional mouse | Conventional rat | Conventional rat[1] | Conventional rat[2] |
|---|---|---|---|---|---|
| S. faecium ADV 1009 | 68.0 | 60.1 | 77.6 | 78.1 | 75.4 |
| S. faecalis ADV 9001 | 63.6 | 57.6 | 66.1 | 55.4 | 67.5 |
| S. durans ADV 3001 | 58.1 | — | 55.3 | — | — |
| S. mitis ADV 7001 | 71.5 | — | — | — | — |
| S. avium AD 2003 | 70.2 | — | — | 61.2 | — |
| S. faecalis ATCC 19433 | 90.0 | — | — | 96.4 | 93.8 |

[1] Cholesterol-loaded diet
[2] Fructose-loaded diet

TABLE 8B

| Strains | Germ-free mouse | Conventional mouse | Conventional rat | Conventional rat[1] | Conventional rat[2] |
|---|---|---|---|---|---|
| S. faecalis ADV 9001 | 56.4 | 54.6 | 60.4 | 48.6 | 58.6 |
| S. durans ADV 3001 | 61.9 | — | 62.6 | — | — |
| S. mitis ADV 7001 | 70.3 | — | — | — | — |
| S. avium AD 2003 | 68.4 | — | — | 61.6 | — |
| S. faecalis ATCC 19433 | 84.4 | — | — | 92.4 | 94.1 |

[1] Cholesterol-loaded diet
[2] Fructose-loaded diet

TABLE 9

| Strains | Germ-free mouse | Conventional mouse | Conventional rat | Conventional rat[1] | Conventional rat[2] |
|---|---|---|---|---|---|
| S. faecalis ADV 9001 | 42.6 | 30.3 | 51.5 | 41.1 | 43.7 |
| S. durans ADV 3001 | — | 33.3 | 48.1 | — | — |
| S. mitis ADV 7001 | 44.3 | — | 50.5 | — | — |
| S. avium AD 2003 | 38.9 | — | 43.2 | — | — |
| S. faecalis ATCC 19433 | 89.0 | — | — | — | — |

[1] Cholesterol-loaded diet
[2] Fructose-loaded diet

Example 6

Living cells of bacteria prepared according to the above-mentioned living cell preparation method were intraperitoneally administered to ICR mice (6 week-old males, average body weight of 30.0±0.7 g) with 0.5 ml of a bacterial suspension containing $9\times10^9$, $9\times10^8$, and $9\times10^7$ cells per mouse (10 mice in each group). Thus, the thanatobiologic observation of mice was carried out for 14 days.

The $LD_{50}$ values (viable cell number/mouse) calculated according to a Behrens-Krärber method are shown in Table 10 below.

TABLE 10

| Strains | $LD_{50}$ |
| --- | --- |
| S. faecium ADV 1009 | $6.3 \times 10^9$ |
| S. faecalis ADV 9001 | $3.8 \times 10^9$ |
| S. avium AD 2003 | $4.2 \times 10^9$ |
| S. durans ADV 3001 | $8.9 \times 10^9$ |

In the case of the dead cells of the above-mentioned strains according to the present invention, the $LD_{50}$ values corresponded to more than $6\times10^{13}$ cells/mouse (intraperitoneal dosage). Both the living and dead cells of the above-mentioned strains according to the present invention were nontoxic in the case of oral administration.

Example 7

Heat-treated powdered cells derived from S. faecium ADV 1009 were orally dosed to conventional rats (10 rats in each group) for 4 weeks at a daily dosage of $10^8$ to $10^{11}$ cells. Then, the serum cholesterol and triglyceride levels were measured to determine a dose response.

The results are shown in Table 11.

TABLE 11

| Administration of dead cells/day | Serum cholesterol (%) | Serum triglyceride (%) |
| --- | --- | --- |
| $10^8$ | 90 | 72 |
| $10^9$ | 76 | 56 |
| $10^{10}$ | 72 | 44 |
| $10^{11}$ | 68 | 35 |
| Control | 100 | 100 |

Example 8

(Pharmaceutical preparations)

1. A 50 mg amount (corresponding to $5\times10^{10}$ cells) of freeze dried powders of S. faecium ADV 1009 living cells prepared according to the above-mentioned living cell preparation method were uniformly mixed with 950 mg of purified starch powder and, then, the tablets were formed for oral administration. This tablet corresponds to a dosage of $10^9$ cells/kg body weight for a human adult having a body weight of 50 kg.

A tablet obtained from 500 mg of the above-mentioned freeze dried powder by mixing with 500 mg of purified starch powder corresponds to a dosage of $10^{10}$ cells/kg body weight.

Thus, the cell products of the present invention can be converted into the desired dosage form having a predetermined activity by mixing with pharmaceutically acceptable carriers based on the above-mentioned standard dosage.

We claim:

1. A method for lowering the serum cholesterol and/or triglyceride level of humans comprising orally administering to said humans a hypocholesterolemically or hypotriglyceridemically effective amount of living cells, dead cells, or a mixture thereof of a microorganism having the identifying characteristics of at least one strain selected from the group consisting of Streptococcus faecium FERM BP-296, Streptococcus faecalis FERM BP-297, Streptococcus avium FERM BP-298, Streptococcus salivalius FERM BP-299, Streptococcus durans FERM BP-300, Streptococcus mitis FERM BP-301, Streptococcus equinus FERM BP-302, and mutants thereof, and a pharmaceutically acceptable carrier therefor.

2. A method in accordance with claim 1 to treat hyperlipedemia.

3. A method in accordance with claim 1 to treat atherosclerosis.

* * * * *